US006887894B2

(12) United States Patent
Krämer et al.

(10) Patent No.: US 6,887,894 B2
(45) Date of Patent: May 3, 2005

(54) USE OF LIPOIC ACID FOR IMPROVING THE BIOAVAILABILITY OF MINERAL SALTS

(75) Inventors: Klaus Krämer, Landau (DE); Martin Jochen Klatt, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 190 days.

(21) Appl. No.: 09/897,922

(22) Filed: Jul. 5, 2001

(65) Prior Publication Data

US 2002/0028796 A1 Mar. 7, 2002

(30) Foreign Application Priority Data

| Jul. 7, 2000 | (DE) | 100 32 601 |
|---|---|---|
| Feb. 26, 2001 | (DE) | 101 09 303 |
| Jul. 7, 2001 | (DE) | 100 32 601 |

(51) Int. Cl.$^7$ .................. A61K 31/385; C07D 327/00
(52) U.S. Cl. ................................. 514/440; 549/3
(58) Field of Search ........................ 549/3; 514/440

(56) References Cited

U.S. PATENT DOCUMENTS

| 5,292,538 A | | 3/1994 | Paul et al. ................ 426/74 |
| 5,463,093 A | * | 10/1995 | Garnett ................... 554/102 |
| 5,569,670 A | * | 10/1996 | Weischer et al. ......... 514/440 |
| 5,650,429 A | * | 7/1997 | Conrad et al. ........... 514/440 |
| 5,693,664 A | * | 12/1997 | Wessel et al. ............ 514/440 |
| 5,705,192 A | * | 1/1998 | Bethge et al. ............ 424/489 |
| 5,925,668 A | * | 7/1999 | Biewenga et al. ........ 514/440 |
| 5,990,152 A | * | 11/1999 | Hettche et al. ........... 514/440 |
| 5,990,153 A | * | 11/1999 | Wood et al. .............. 514/440 |
| 6,046,228 A | * | 4/2000 | Rice et al. ................ 514/441 |
| 6,127,394 A | * | 10/2000 | Pershadsingh et al. ... 514/369 |
| 6,235,772 B1 | * | 5/2001 | Packer et al. ............ 514/440 |
| 6,271,254 B1 | * | 8/2001 | Ulrich et al. ............. 514/440 |
| 6,288,106 B1 | * | 9/2001 | Pearson et al. .......... 514/440 |
| 6,313,164 B1 | * | 11/2001 | Fujita et al. ............. 514/440 |
| 6,331,559 B1 | * | 12/2001 | Bingham et al. ........ 514/440 |
| 6,348,490 B1 | | 2/2002 | Hettche et al. ........... 514/440 |
| 6,369,098 B1 | * | 4/2002 | Pershadsingh et al. ... 514/440 |

FOREIGN PATENT DOCUMENTS

| DE | 1668887 | 7/1971 |
| DE | 4419783 | 12/1995 |
| EP | 702953 | 3/1996 |
| FR | 6518 | 12/1968 |
| WO | 01/66560 | 9/2001 |

OTHER PUBLICATIONS

Roth et al. "Zn–Bindungskapazität des Serums. Ein Parameter zur Diagnose von marginalem Zn–Mangel" Res. Exp. Med. vol. 177 (1980) pp. 213–219.
Sigel "Die hydrophoben und Metallonen–koordinierenden Eigenschaften von α–Liponsäure—ein Biespiel Für intramoleckulare Gleichgewichte in Metallionen–Komplexen" Angew. Chem. vol. 91 (1982) pp. 421–432.

McCormick et al. "Stability and Structure of Binary and Ternary Complexes of α–Lipoate and Lipoate Derivatives with $Mn^{2+}$, and $n^{2+}$ in Solution[1]" Archives of Biochemistry and Biophysics vol. 187 (1978) pp. 208–214.
Bonomi et al. "Molecular Aspects of the Removal of Ferritin–bound iron by DL–dihydrolipoate" Biochimica et Biophysica Acta vol. 994 (1989) pp. 180–186.
Strasdeit et al. "Coordination Chemistry of Lipoic Acid and Related Compounds, Part 1 Synthesis and Crystal Structures of the UV– and Light Sensitive Lipoato Complexes $[M(lip)_2(H_2O)_2]$ (M=Zn, Cd)" Z. Narurforsch 52b (1997) pp. 17–24.
Brown et al. "The Reactions of 1,3–Dimercaptopropane, Lipoic Acid and Dihydrolipoic Acid with Metal Ions" J. Inorg. Nucl. Chem. vol. 32 (1970) pp. 2671–2675.
Seal et al. "Effect of Dietary Picolinic Acid on the Metabolism of Exogenous and Endogenous Zinc in the Rat[1]" J. Nutr. vol. 115 (1985) pp. 986–993.
Schwartz et al. "Zum Einfluβ von Bkiloinsäure und Zitronensäure auf die intestinale Zin–Absorption in vitro und in vivo" Res. Exp. Med vol. 182 (1983) pp. 39–48.
Welch et al. "Effects of Oxalic Acid on Availability of Zinc from Spinach Leaves and Zinc Sulfate to Rats" J. Nutr. vol. 107 (1977) pp. 929–933.
King et al. "Absorption of Stable Isotopes of Iron, Copper, and Zinc during Oral Contraceptive Use" Am. J. of Clin. Nutrition vol. 31 (1978) pp. 1198–1203.
Solomons et al. "Studies on the Bioavailabity of Zinc in man III. Effects of ascorbic acid on zinc absorption" Am J. Clin. Nutrition vol. 32 (1979) pp. 2495–2499.
Sandström et al. "Effect of Ascorbic Acid on the Absorption of Zinc and Calcium in Man" Int. J Vit. Nutr. Res 57 (1987) pp. 87–90.
Palluf et al. "Effekt einer abgestuften Zn–Zufuhr und Zulagen von Cotronensäure zu einer Mais–Soja–Diät auf Leistungparameter und Mineralstoffverwertung beim Ferkel[1]" J. Amin. Physionl. a. Anim Nutr. vol. 71 (1994) pp. 189–199.
Palluf et al. "Effekt einer Zulage an Citronensäure auf die bioverfügbarkeit von Zink aus Maiskeimen" Z Ernährungswis vol. 29 (1990) pp. 27–38.
Chen et al. "In Vitro Bone Resorption Is Dependent on Physiological Concentations of Zinc" Biological Trace Element Research vol. 61 (1998) pp. 9–18.

(Continued)

Primary Examiner—Deborah Lambkin
(74) Attorney, Agent, or Firm—Keil & Weinkauf

(57) ABSTRACT

The use of α-lipoic acid or α-dihydrolipoic acid for increasing the bioavailability of mineral salts, the use of α-lipoic acid or α-dihydrolipoic acid in combination with metal salts, in particular the use of metal α-lipoates, metal α-dihydrolipoates or metal-α-lipoic acid complexes, in particular in mineral preparations or drugs and the metal α-lipoates, metal α-dihydrolipoates or metal-α-lipoic acid complexes themselves are described.

17 Claims, 4 Drawing Sheets

OTHER PUBLICATIONS

Rojas et al. "Relative Bioavailiabity of Two Organic and Two Inorganic Zinc Sources Fed to Sheep" J. Animal Science vol. 75 (1995) pp. 1202–1207.

Wedekind et al. "Bioavailability of Zinc from Inorganic and Organic Sources for Pigs Fed Con–Soybean Meal Diets" J. Anim. Sci. vol. 72 (1994) pp. 2681–2689.

Wedekind et al. "Methodology for Assessing Zinc Bioavaialability: Efficacy Estimates for Zinc–Methionine Zinc Sulfate, and Zinc Oxide" J. Anim. Sci. vol. 70 (1992) pp. 178–187.

* cited by examiner

USE OF LIPOIC ACID FOR IMPROVING THE BIOAVAILABILITY OF MINERAL SALTS

The present invention relates to the use of α-lipoic acid or α-dihydrolipoic acid for increasing the bioavailability of mineral salts, the use of α-lipoic acid or α-dihydrolipoic acid in combination with metal salts, in particular the use of metal α-lipoates, metal α-dihydrolipoates or metal-α-lipoic acid complexes, in particular in mineral preparations or drugs and the metal α-lipoates, metal α-dihydrolipoates or metal-α-lipoic acid complexes themselves.

Minerals are the constituents of plant and animal tissues which remain as ash in combustion. Depending on the content of the individual elements, minerals are classified as major elements, for example Ca, P, K, Cl, Na, Mg, or as trace elements, for example Fe, Zn, Cu, Mn, V, Se, Mn, I, Sn, Ni, Mo, Cr, Co.

The metallic minerals are absorbed by human or animal organisms as cations, generally as mineral salts together with inorganic anions. The essential metallic minerals having a known biological function in the organism have very varied functions in the organism, for example as electrolytes, constituents of enzymes or as building blocks of certain bodily substances.

Mineral salts for supplementation or therapy of mineral deficiencies in human or animal organisms should have as high a bioavailability as possible.

It is known that it is possible to increase the bioavailability of zinc salts over $ZnSO_4$ by completing with proteinate (B. A. Reiling et al., J. of Animal Science 70 (1992), Supplement 1, 84th Annual Meeting, Abstract 649).

It is also known that complexing or salt formation of zinc salts with methionine leads to an increased bioavailability of $Zn^{2+}$ in chickens (Wedekind, J. Anim. Sci. 70 (1992), p. 176).

In contrast, it has been found in the pig model that the bioavailability of the organic salts of zinc with methionine or lysine is poorer than that of the inorganic $ZnSO_4.H_2O$ (Wedekind et al., J. Anim. Sci. 72 (1994), pp. 2681 to 2689).

Other studies with $ZnCl_2$, ZnMet and zinc propionate found roughly comparable bioavailability of $Zn^{2+}$ from organic or inorganic sources (Beutler et al., Biological Trace Element research, 61 (1998), page 19), even though Rojas et al. found a slightly increased bioavailability of the organic zinc salts ZnMet or ZnLys compared with $ZnSO_4$ in sheep (J. Anim. Sci. 73 (1995), pp. 1202 to 1207).

For citric acid, a positive effect on Zn bioavailability is described. Thus, in growing rats with a suboptimal alimentary Zn supply, by adding 1% citric acid to phytic-acid-rich corn-germ-based diets, a moderate improvement in Zn status (plasma Zn concentration, alkaline phosphatase activity, metallothioneine concentration in the jejunum) is achieved (Pallauf et al., Z. Ernährungswiss. 29 (1990), pages 27 to 38).

Comparable positive effects of citric acid on Zn utilization have also been found in pigs (Pallauf et al., J. Anim. Physiol. a. Anim. Nutr. 71 (1994), pages 189 to 199).

Ascorbic acid increases the bioavailability of inorganic iron (Hallberg et al., Hum. Nutr. Appl. Nutr. 40A (1986), 97 to 113). In contrast thereto, ascorbic acid does not change the bioavailability of dietary zinc, or changes it only very slightly (Sandström and Lederblad, Int. J. Vitamin Nutr. Res. 57 (1987), 87 to 90, Solmons et al., Am. J. Clin. Nutr. 32 (1979), 2495 to 2499).

The results of previous studies on the effects of oxalic acid (Kelsay et al., Am. J. Clin. Nutr. 31 (1983), 1198 to 1203; Welch et al., J. Nutr. 107 (1977), 929 to 933), and picolinic acid (Schwarz et al., Res. Exp. Med. 182 (1983), 39 to 48; Seal et al., J. Nutr. 115 (1985), 986 to 993), on Zn bioavailability are not uniform and do not permit any clear conclusions to be drawn.

The metal complexes or salts or mineral salts and organic chelators used in the prior art thus lead to increased bioavailability only within limitations, so that there is a great need for novel compounds and novel organic chelators or salts which lead to increased bioavailability of mineral cations, compared with the inorganic mineral salts.

It is an object of the present invention, therefore, to provide novel organic chelators and complexing agents or salt-forming agents and novel organic mineral compounds which have an increased bioavailability compared with the inorganic mineral salts, fewer disadvantages than the prior art and further advantages.

We have found that this object is achieved by using α-lipoic acid or α-dihydrolipoic acid to increase the bioavailability of mineral salts.

Figure 1:
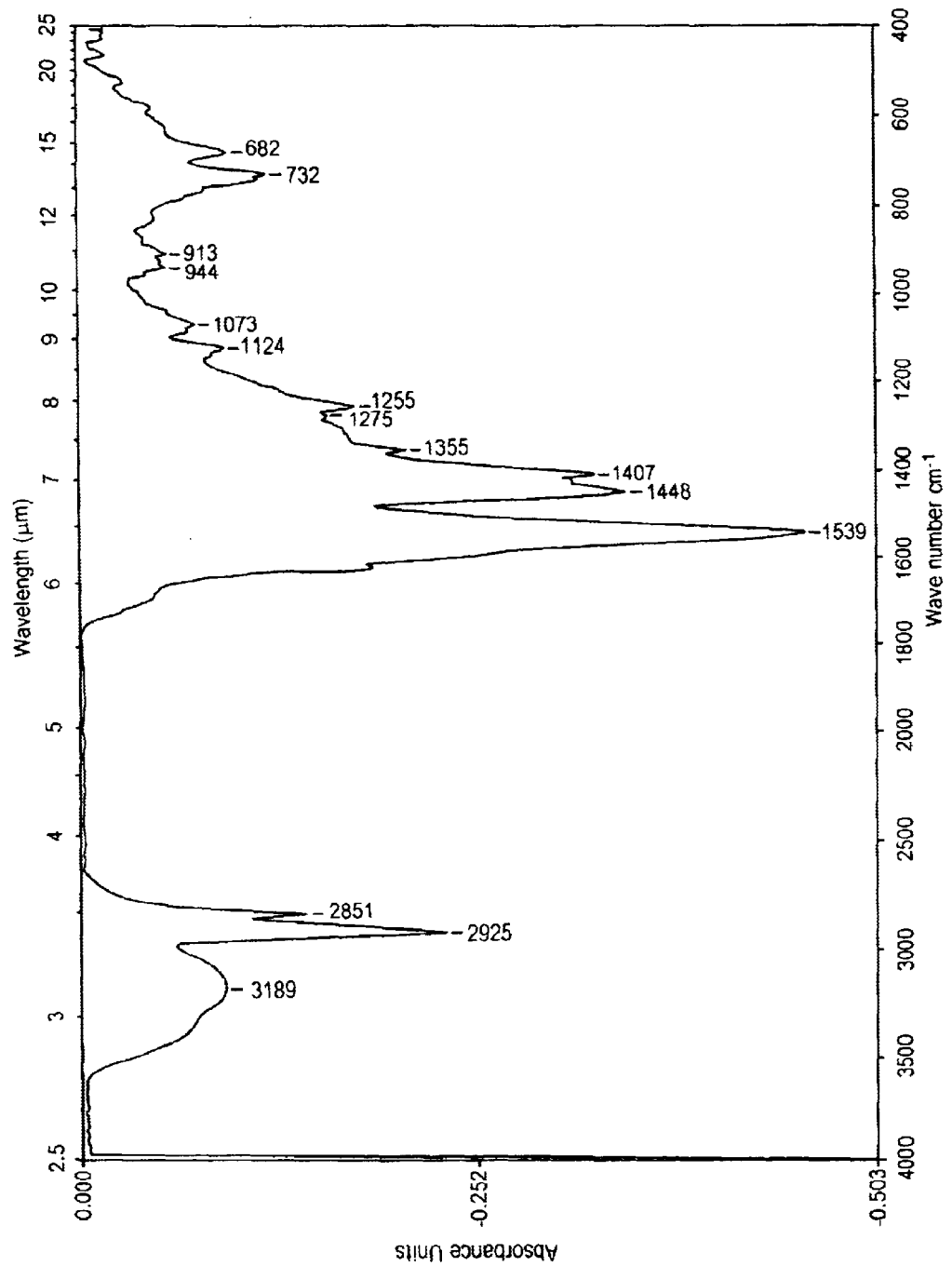
FIG. 1 is an IR(KBr) plot of absorbance units as a function of wavelength, based on the results of Example 2 herein.
Figure 2:
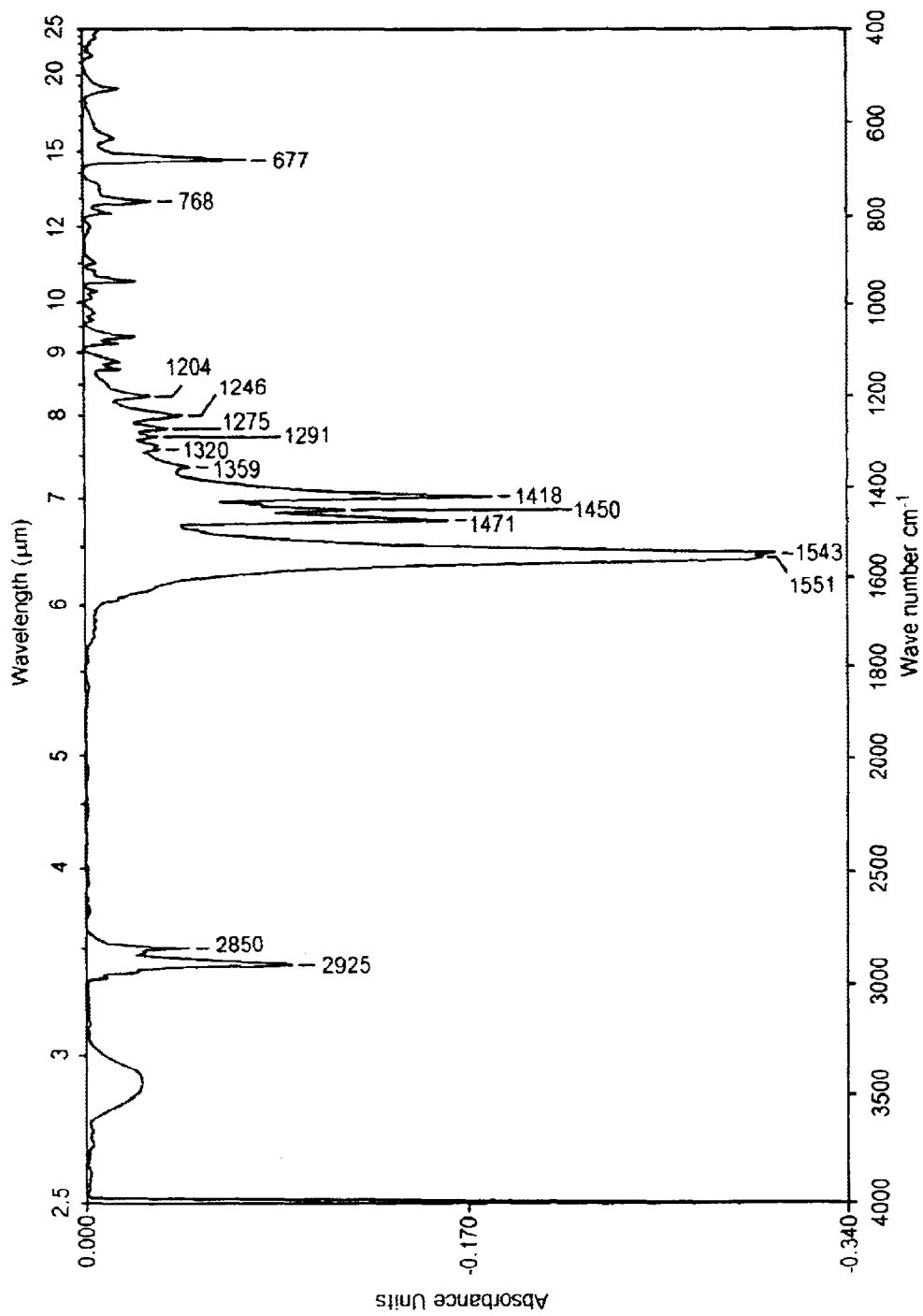
FIG. 2 is an IR(KBr) plot of absorbance units as a function of wavelength, based on the results of Example 1 herein.

For the purposes of the present invention, the bioavailability of a compound is the proportion of a compound which, after oral administration, is absorbed in the intestine and appears via the liver unchanged in the blood circulation or the intestinal digestion and absorption of a compound, that is the apparent absorption or, taking into account the endogenous losses, the true absorption, in which case, when the true absorption versus the apparent absorption is determined, account is taen of the amount of a compound which has already been absorbed at an earlier time point and is excreted via secretion mechanisms and intestinal sloughing (endogenous losses) and is also excreted with the feces, or after correction for renal excretion a balance is determined or a sequence of metabolic events which, in addition to digestion, solubility, absorption and distribution comprises organ uptake and release and enzymatic transformation, secretion mechanisms and excretion mechanisms and can thus adopt metabolic functions, in the form of cofactors for enzymes and hormones and stabilization of membrane lipid and structural proteins, which mean, for example, that enzymatic activities are increased or the accumulation of a compound in organs such as liver and bones.

For the purposes of the present invention, an increased bioavailability of a mineral salt is an improvement in at least one of the abovedescribed bioavailability parameters, compared with an inorganic mineral salt, for example a sulfate or halide.

For the purposes of the present invention, α-lipoic acid is racemic α-lipoic acid or α-lipoates or enantiomerically pure (R)- or (S)-α-lipoic acid or (R)- or (S)-α-lipoates, α-dihydrolipoic acid is racemic α-dihydrolipoic acid or α-dihydrolipoates or enantiomerically pure (R)- or (S)-α-dihydrolipoic acid or (R)- or (S)-α-dihydrolipoates.

"Racemic"is not only a 1:1 mixture of the two enantiomers but also enriched enantiomers which can occur in different ratios, for example in a ratio of 99:1.

In a preferred embodiment, the bioavailabiolity of mineral salts is increased by using at least one mineral salt in combination with α-lipoic acid or α-dihydrolipoic acid.

Mineral salts are salts of physiologically acceptable monovalent to trivalent metals.

Preferred mineral salts whose bioavailability is increased in combination with α-lipoic acid or α-dihydrolipoic acid are mineral salts of the formula I, $$(M)_n(B)_m \qquad \qquad I$$

where
M is a monovalent to trivalent physiologically acceptable metal cation,
B is a monovalent to trivalent physiologically acceptable anion,
n is 1, 2 or 3 and
m is 1, 2 or 3,
where the subscripts n and m correspond to the valency and charge equalization of the mineral salt of the formula I.

Preferred physiologically acceptable monovalent to trivalent metal cations M are the essential metal cations, for example $Na^+$, $K^+$, $Mg^{2+}$, $Ca^{2+}$, $Fe^{2+}$, $Fe^{3+}$, $Sn^{2+}$, $Zn^{2+}$, $Cu^{2+}$, $Mn^{2+}$, $Mn^{3+}$, $Cr^{3+}$, $Mo^{3+}$, $Co^{2+}$ or $Ni^{2+}$.

Preferred physiologically acceptable monovalent to trivalent anions B are, for example, inorganic anions, in particular halides such as $F^-$ or $Cl^-$, chalcogenides, for example $O^{2-}$, or the anions, $NO_{3-}$, $SO_4^{2-}$, $CO_3^{2-}$, $PO_4^{3-}$, $HCO_{3-}$, $HPO_4^{2-}$, $H_2PO_{4-}$, or the organic anions ascorbate, oxalate, citrate, gluconate, picolinate, aspartate, histidinate, saccharate, orotate, lactobionate, lactate, fumarate, formate, acetate, glucobionate, glucocephate or also, for example, the anions α-lipoate or α-dihydrolipoate described below.

The combined use of at least one mineral salt together with α-lipoic acid or α-dihydrolipoic acid increases the bioavailability of the mineral salt.

For the purposes of the present invention, combination is taken to mean the simultaneous administration, or administration offset in time and/or space of at least one mineral salt and α-lipoic acid or α-dihydrolipoic acid. For example, at least one mineral salt and α-lipoic acid or α-dihydrolipoic acid can be administered together in one formulation, for example a mineral preparation or a drug preparation.

In a particularly preferred embodiment, α-lipoic acid, in particular (R)-α-lipoic acid is used in the abovedescribed combination with mineral salts, preferably mineral salts of the formula I.

The invention also relates to a preparation, in particular a mineral preparation or a drug preparation, comprising at least one mineral salt and (R)-α-lipoic acid or (S)-α-lipoic acid, preferably (R)-α-lipoic acid. Preferably, the proportion of the one enantiomer in the presence of the other enantiomer is at least 70 mol %, in comparison with the other enantiomer.

A mineral preparation can, for example, comprise other mineral salts, formulation aids and may or may not also comprise vitamins or vitamin mixtures.

A drug preparation can comprise, for example, further active ingredients and aids, for example fillers, preservatives, tablet disintegrants, flow controllers, softeners, wetting agents, dispersants, emulsifiers, solvents, retarding agents or antioxidants (cf. H. Sucker et al.,: Pharmazeutische Technologie [Pharmaceutical Technology], Thieme-Verlag, Stuttgart, 1991).

The amounts in which the α-lipoic acid or α-dihydrolipoic acid is used in relation to a mineral salt are not critical and depend on the physiologically acceptable amount. Typically, the α-lipoic acid or α-dihydrolipoic acid is used in a molar ratio to a mineral salt of from 0.1:1 to 1000:1.

In a preferred embodiment, metal α-lipoates, metal α-dihydrolipoates or metal-α-lipoic acid complexes are used directly as combination, that is to say as mineral salt with increased bioavailability.

These compounds have an increased bioavailability.

These compounds have the further advantage that the metallic mineral and the therapeutically valauble lipoic acid are present in one formulation. These compounds are therefore particularly useful as space-saving ingredients in cosmetic formulations, in drug formulations and in formulations of feed and food supplements, in particular in solid administration forms.

In a preferred embodiment, the metal α-lipoates, metal α-dihydrolipoates or metal-α-lipoic acid complexes of the formula II can be used as minerals having an increased bioavailability, $$(M)_w(Lp)_x(A)_y(H_2O)_z \qquad \qquad II$$

where
M is a monovalent to trivalent physiologically acceptable metal cation or a mixture of monovalent to trivalent physiologically acceptable metal cations,
Lp is racemic α-lipoic acid or α-dihydrolipoic acid, (R)- or (S)-α-lipoic acid or (R)- or (S)-α-dihydrolipoic acid, racemic α-lipoate or dihydro-α-lipoate or (R)- or (S)-α-lipoate or (R)- or (S)-dihydro-α-lipoate,
A is a physiologically acceptable monovalent or divalent anion,
w is 1 or 2
x is 1, 2, 3 or 4,
y is 0, 1, 2 or 3 and
z is 0, 1, 2, 3, 4, 5 or 6,
where the subscripts w, x and y correspond to the valency and charge equalization.

Preferred physiologically acceptable monovalent to trivalent metal cations M are, as described above, the essential metal cations, for example $Na^+$, $K^+$, $Mg^{2+}$, $Ca^{2+}$, $Fe^{2+}$, $Fe^{3+}$, $Sn^{2+}$, $Zn^{2+}Cu^{2+}$, $Mn^{2+}$, $Mn^{3+}$, $Cr^{3+}$, $Mo^{3+}$, $Co^{2+}$ or $Ni^{2+}$, in particular $Zn^{2+}Fe^{2+}$, $Fe^{3+}$, $Ca^{2+}$, $Mn^{3+}$ or $Cr^{3+}$.

α-Lipoic acid or its reduced form, α-dihydrolipoic acid, enters into salt-like ionic bonds and/or coordinate bonds via the carboxyl oxygen or the closed or open disulfide unit, together with metals as anions (α-lipoate: single negative charge; α-dihydrolipoate: single or double negative charge). α-Lipoic acid or α-dihydrolipoic acid can also have coordinate bonds to metal cations as a neutral molecule. They can be used either as racemate or else as enantiomerically pure in the (R)- or (S)-form.

Preferred physiologically acceptable monovalent to divalent anions A are, for example, inorganic anions, in particular halides, such as $F^-$ or $Cl^-$, chalcogenides, for example $O^{2-}$— or the anions $NO_3$—, $SO_4^2$—, $CO_3^2$—, $HCO_3$—, $HPO_4^2$—, $H_2PO_4$— or the organic anions ascorbate, oxalate, citrate, gluconate, picolinate, aspartate, histidinate, saccharate, orotate, lactobionate, lactate, fumarate, formate, acetate, glucobionate or glucocephate.

In the compounds of the formula II, up to 6 molecules of water may be bound by coordinate bonds, preferably up to 4 molelcules of water, in particular up to two molecules of water.

In preferred compounds of the formula II, the remainder of Lp used are α-lipoates, in particular (R)-α-lipoates and the content of other anions A is 0 (y=0). In this preferred embodiment, the subscripts w and x correspond to the valency and charge equalization of the compounds of the formula II.

It can be advantageous to use the compounds of the formula II in combination with α-lipoic acid or α-dihydrolipoic acid, for example to further increase the bioavailability.

The invention therefore further relates to a preparation comprising compounds of the formula II, preferably compounds of the formula II', and α-lipoic acid or α-dihydrolipoic acid.

Siegel et al., describe, in a structural study, binary complexes of Mn, Cu, Zn, Cd and Pb with racemic and (R)- and (S)-lipoates (Archives of Biochemistry and Biophysics 187 (1978), pages 208 to 214; Angew. Chem. 94 (1982), 421–432).

P. R. Brown et al., describe, in further structural studies, a binary complex of Hg with racemic α-lipoic acid, with the lipoic acid being bound by coordination as a neutral molecule. In addition, binary complexes of Hg and Ni with racemic divalent negatively charged α-dihydrolipoate are described. The structural descriptions served for investigation of the use of lipoic acid to treat heavy metal poisoning (J. Inorg. Nucl. Chem. 32 (1970), 2671 to 2675).

Bonomi et al., describe a complex of Fe with racemic α-dihydrolipoic acid for investigation of the use of dihydrolipoic acid for removing ferritin-bound iron (Biochemica et Biophysica Acta. 994 (1989), 180 to 186).

In a further structural study, Strasdeit et al., describe complexes of Zn and Cd with monovalent negatively charged racemic α-lipoates, with two molecules of water being coordinated to the central atom (Z. Naturforsch. 52b (1997), 17 to 24).

The invention therefore relates to the novel metal α-lipoates, metal α-dihydrolipoates or metal-α-lipoic acid complexes of the formula II',

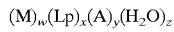

where
M is a monovalent to trivalent physiologically acceptable metal cation or a mixture of monovalent to trivalent physiologically acceptable metal cations,
Lp is racemic α-lipoic acid or α-dihydrolipoic acid, (R)- or (S)-α-lipoic acid or (R)- or (S)-α-dihydrolipoic acid, racemic α-lipoate or dihydro-α-lipoate or (R)- or (S)-α-lipoate or (R)- or (S)-dihydro-α-lipoate,
A is a physiologically acceptable monovalent or divalent anion,
w is 1 or 2,
x is 1, 2, 3 or 4,
y is 0, 1, 2 or 3 and
z is 0, 1, 2, 3, 4, 5 or 6,
where the subscripts w, x and y correspond to the valency and charge equalization and the following compounds are excluded:

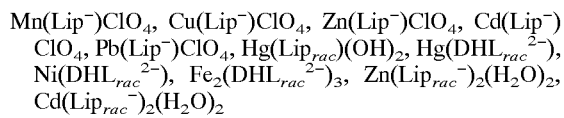

where
$Lip^-$ is monovalent negative racemic or (R)- or (S)-α-lipoate,
$Lip_{rac}^-$ is monovalent negative racemic α-lipoate,
$Lip_{rac}$ is racemic α-lipoic acid and
$DHL_{rac}^{2-}$ is divalent negative racemic α-dihydrolipoate.

The compounds of the formula II' correspond, in the preferred embodiments also, except for the excluded compounds, to the compounds of the formula II described above.

The invention further relates to a preparation, in particular a mineral preparation or a drug preparation, comprising metal α-lipoates, metal α-dihydrolipoates or metal-α-lipoic acid complexes of the formula II'.

A mineral preparation can comprise, for example, further mineral salts, formulation aids, for example fillers, dyes and, if appropriate, also vitamins or vitamin mixtures. The dosage of the individual components depends on the desired content, which can be a function, for example, of the recommended daily intake and depending on whether the mineral preparation is to be used, for example, as food supplement, food substitute or feed supplement.

A drug preparation can comprise, for example, further active compounds and aids, for example fillers, preservatives, tablet disintegrants, flow control agents, softeners, wetting agents, dispersants, emulsifiers, solvents, retarding aids or antioxidants, and also aids which are known per se for a parenteral or enteral application (see S. Sucker et al.,: Pharmazeutische Technologie [Pharmaceutical Technology], Thieme-Verlag, Stuttgart, 1991).

The invention further relates to the use of the metal α-lipoates, metal α-dihydrolipoates or metal-α-lipoic acid complexes of the formula II as feed-stuff or food supplements.

The compounds of the formula II, furthermore, represent in one source an antioxidant activity and a supply of minerals. They can therefore also be used in cosmetic formulations.

Therefore, the invention further relates to the use of the compounds of the formula II in cosmetic formulations.

The invention further relates to the metal α-lipoates, metal α-dihydrolipoates or metal-α-lipoic acid complexes of the formula II for use as drugs.

The metal α-lipoates, metal α-dihydrolipoates or metal-α-lipoic acid complexes of the formula II can be used for preparing a drug for treating disorders in which lipoic acid has a therapeutic or prophylactic effect and there is a mineral salt deficiency.

For example, α-lipoic acid, in particular (R)-α-lipoic acid acts as an insulin sensitizer in the prevention and therapy of diabetes mellitus. Furthermore, lipoic acid is used therapeutically in diabetic polyneuropathy. Diabetics frequently have a mineral salt deficiency, in particular a zinc deficiency.

The metal α-lipoates, metal α-dihydrolipoates or metal-α-lipoic acid complexes of the formula II can thus be used to treat diabetes, and furthermore for treating tumors, HIV infections, AIDS, renal insufficiency, malnutrition, protein-energy malnutrition and mineral deficiencies.

Mineral deficiencies can be caused, for example, by malnutrition, unbalanced nutrition, drug intake, for example taking of diuretics, diarrhea, alcohol consumption, parenteral or enteral nutrition, trauma(OP), loss of blood or antagonisms by other dietary constituents, for example phytate, dietary fibers, or excess oxalate or phosphate.

The metal α-lipoates, metal α-dihydrolipoates or metal-α-lipoic acid complexes of the formula II can be prepared in a manner known per se, for example as in Siegel et al., Archives of Biochemistry and Biophysics 187 (1978), pages 208 to 214; Angew. Chem. 94 (1982), 421–432; P. R. Brown et al., J. Inorg. Nucl. Chem. 32 (1970), 2671 to 2675; Bonomi et al., Biochemica et Biophysica Acta 994 (1989), 180 to 186 and Strasdeit et al., Z. Naturforsch. 52b (1997), 17 to 24.

Preferably, they are prepared by reacting alkali metal salts of α-lipoic acid or α-dihydrolipoic acid in solution, preferably in aqueous methanolic solution, with mineral salts and subsequent crystallization.

The use of α-lipoic acid or α-dihydrolipoic acid for increasing the bioavailability of mineral salts and the inventive compounds have further advantages compared with customary inorganic mineral sources, such as

- increasing the live weight gain and feed/nutrient intake by test subjects, in particular animals,
- increasing the mineral salt availability and mineral salt status, in particular increasing the mineral salt intake, increasing the absolute apparent absorption and apparent absorption of mineral salts, increasing the mineral salt deposition in femur tissue and the mineral salt concentration in the plasma, increasing alkaline phosphatase activity and increasing hepatic metallothionine concentration.

The examples below illustrate the invention:

EXAMPLE 1

Synthesis of $Zn((R)\text{-}\alpha\text{-lipoate})_2(H_2O)_2$ 2.06 g (10 mmol) of (R)-α-lipoic acid were dissolved in 150 ml of methanol and at room temperature a solution of 0.4 g (10 mmol) of NaOH in 50 ml of water was added with stirring.

1.49 g (5 mmol) of zinc nitrate were rapidly added to 150 ml of methanol to dissolve the sodium salt and the solution was stirred for a further two hours.

The clear pale-yellow solution was transferred to a Petri dish. After evaporating off the solvent, a yellow precipitate was obtained which was carefully washed with water and toluene and dried overnight in a countercurrent nitrogen stream.

The resulting zinc complex was analytically pure.

Figure 3A:
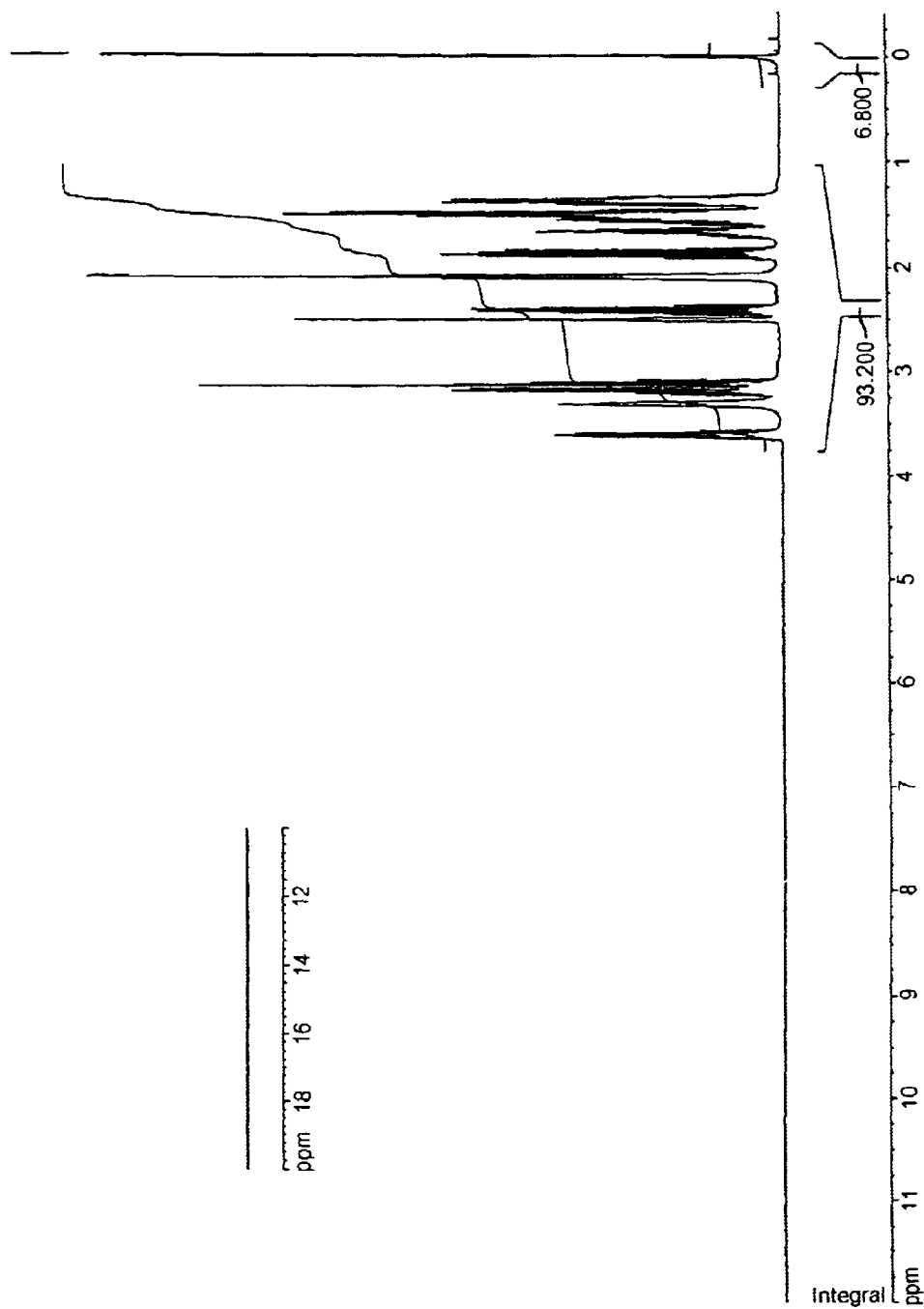
FIGS. 3a and 3b depict the $^1$H-NMR and $^{13}$C-NMR, respectively, for the product of Example 1 herein.
Figure 3B:
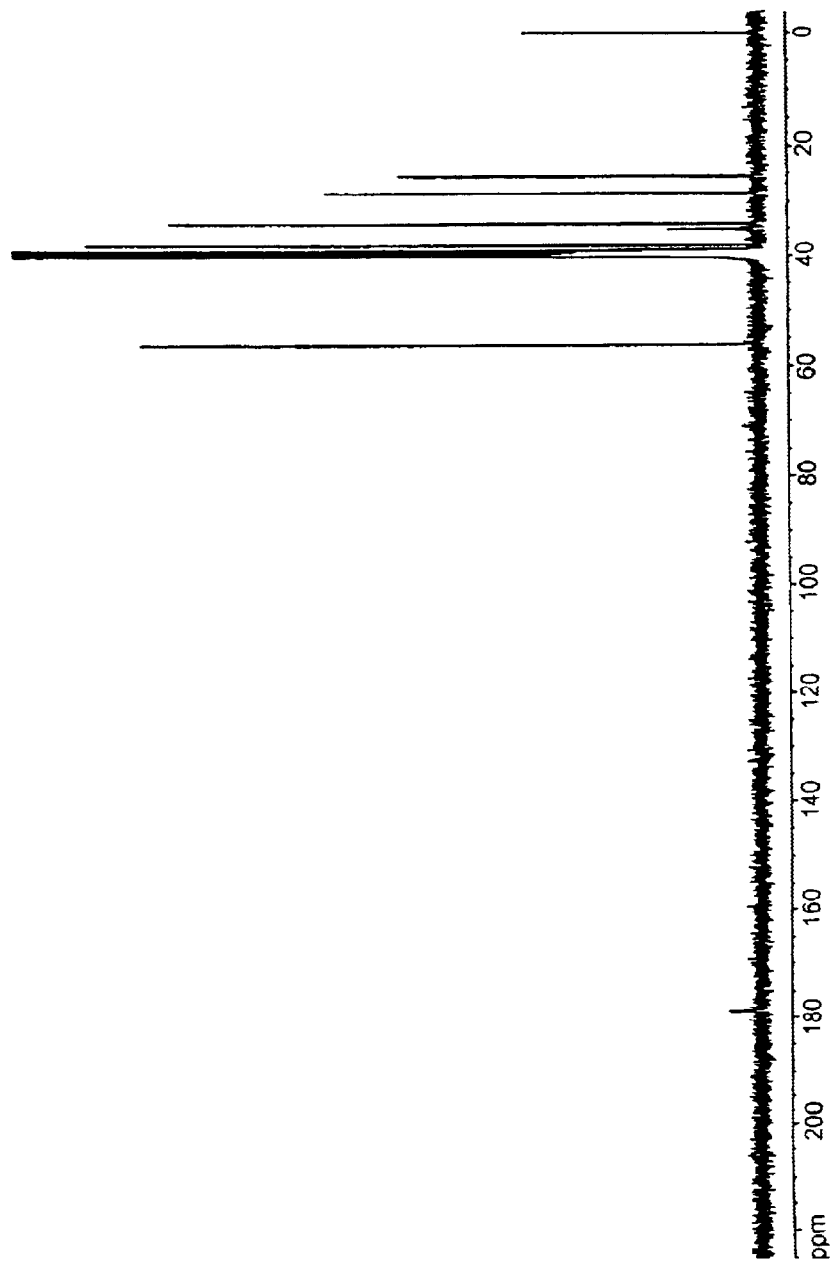

| Yield: | 4.55 g (89% of theory) |
|---|---|
| Melting point: | 123° C. |
| $^1$H-NMR/$^{13}$C-NMR | see Table 2, Table 3 and FIG. 3a ($^1$H) and 3b ($^{13}$C) |

EXAMPLE 2

Synthesis of $Zn((rac)\text{-}\alpha\text{-lipoate})_2(H_2O)_2$

The synthesis was performed in a similar manner to Example 1 using racemic α-lipoic acid. Yellow needles.

| Yield: | 92% of theory |
|---|---|
| Melting point: | 112° C. |
| $^1$H-NMR/$^{13}$C-NMR | see Table 2, Table 3 IR(KBr) see FIG. 1 |

The Zn complexes of Examples 1 and 2 were also prepared starting from zinc acetate, zinc sulfate and zinc chloride and produced the compounds of Examples 1 and 2 in comparable yields and purities.

TABLE 1

$^{13}$C-NMR spectra (D$^6$-DMSO, data in [ppm]) for Examples 1 and 2

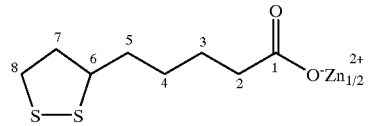

| C atom No. | $Zn((rac)\text{-}\alpha\text{-lipoate})_2$ $(H_2O)_2$ (Example 2) | $Zn((R)\text{-}\alpha\text{-lipoate})_2(H_2O)_2$ (Example 1) |
|---|---|---|
| 1 | 178 | 178 |
| 2 | 39 | 39 |
| 3 | 25 | 25 |
| 4 | 28 | 28 |
| 5 | 37 | 35 |
| 6 | 56 | 56 |
| 7 | 34 | 34 |
| 8 | 40 | 40 |

TABLE 2

$^1$H-NMR spectra (D$^6$-DMSO, data in [ppm]) for Examples 1 and 2

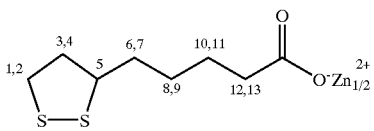

| H atom No. | $Zn((rac)\text{-}\alpha\text{-lipoate})_2$ $(H_2O)_2$ (Example 2) | $Zn((R)\text{-}\alpha\text{-lipoate})_2(H_2O)_2$ (Example 1) |
|---|---|---|
| 1.2 | 3.15 (m) | 3.15 (m) |
| 3.4 | 2.45 (m) | 2.45 (m) |
| 5 | 3.65 (m) | 3.65 (m) |
| 6–11 | 1–2 | 1–2 |
| 12.13 | 2.05 (t) | 2.05 (t) |

EXAMPLE 3

Preparation of Further Metal (R)-α-lipoates

The synthesis was performed in a similar manner to Example 1 using differing mineral salts. The results are summarized in Table 3.

TABLE 3

| Example | Mineral salt used | Color of the metal (R)-α-lipoate | Yield of the metal (R)-α-lipoate |
|---|---|---|---|
| 3.1 | Fe(NO$_3$)$_3$ | light brown | 48% |
| 3.2 | Cu(NO$_3$)$_2$ | turquoise | 84% |
| 3.3 | Cr(NO$_3$)$_3$ | blue | 59% |
| 3.4 | MnCl$_2$ | beige | 60% |
| 3.5 | Co(NO$_3$)$_2$ | violet | 45% |
| 3.6 | Ca(OH)$_2$ | white | 68% |

II. Biological Examples

Bioavailability investigations of $Zn((R)\text{-}\alpha\text{-lipoate})_2(H_2O)_2$ in rats compared with the bioavailability of zinc sulfate General Conditions Zinc is generally better utilized from foods of animal origin than from plant products. The main reason for this is considered to be the higher phytic acid content (PA) in plant products. Zinc is the trace element whose bioavailability most markedly decreases with a high PA intake. Phytic acid (PA) does not decrease the bioavailability of dietary zinc alone, but, to a great extent, Zn secreted endogenously is also removed from reabsorption. From a molar PA:Zn ratio>from 10 to 15 in the diet, under controlled conditions in rats, a reduced Zn bioavailability is to be expected.

To take into account this effect of natural phytic acid content in feeds or foods, in the experimental diets, in addition to a PA-free diet, diets with supplemented PA were also used.

NaPA hereinafter means sodium phytate, AAS is atomic absorption spectrometry, IM is initial mass, FW is fresh weight, HPLC is high performance liquid chromatography, ICP-AES is inductively coupled plasma atomic emission spectrometry, LW is live weight, MT is metallothionin, n.d. is not detectable and PE is polyethylene.

EXAMPLE 4

Study 1: Bioavailability Investigations of $Zn((R)-\alpha\text{-lipoate})_2(H_2O)_2$ in Rats 4.1 Origin and housing conditions of the experimental animals and metabolic study procedure Male Albino rats (Wistar) of an initial weight of 40 g were used. The animals were kept during each 28-day experimental period at a room temperature of 22° C., a relative humidity of approximately 55% and in a 12-hour light-dark cycle. The rats were housed individually in Makrolon cages with stainless steel bottoms which permitted controlled feed intake and quantitative collection of feces and urine. The feed was provided once a day at $8^{00}$. The live mass of the rats was determined weekly, feces and urine were collected every day at $10^{00}$ and $17^{00}$. At the end of the experiment, the rats were decapitated after chloroform anesthesia.

4.2 Description of the diets and experimental design

To achieve defined mineral salt concentrations and PA concentrations, an experimental diet was prepared on the basis of high-purity individual components (Table 4), which was used to feed the zinc lipoate $Zn((R)-\alpha\text{-lipoate})_2(H_2O)_2$ from Example 1 and PA.

Minerals, trace elements and vitamins were supplemented on the basis of NRC recommendations (1978). No account was taken of the native vitamin contents of the individual components. To avoid any amino acid imbalances owing to the high content of sulfur amino acids in egg white protein, synthetic L-lysine was supplemented.

TABLE 4

| Component | g/kg |
|---|---|
| Corn starch | 477 |
| Egg white protein | 200 |
| Sucrose | 100 |
| Soybean oil | 70 |
| Cellulose | 30 |
| L-lysine HCl | 3 |
| Mineral premix[1] | 100 |
| Vitamin premix[2] | 20 |

[1]Mineral premix (quantities per kg of diet) 26.73 g of $CaHPO_4.2 H_2O$ high purity; 6.68 $KH_2PO_4$ high purity; 5.07 g; $MgSO_4.7 H_2O$ high purity; 4.43 g of $CaCO_3$ high purity; 2.47 g of NaCl high purity 1.22 g of $Na_2CO_3$ high purity; 298.68 mg of $FeSO_4.7 H_2O$ of analytical purity; 184.59 mg of $MnSo_4.H_2O$ of analytical purity; 87.99 mg of $ZnSO_4.7 H_2O$ of analytical purity; 27.50 mg of $CuSO_4.5 H_2O$ of analytical purity; 4.41 mg of $Cr(CH_3COO)_3$ of analytical purity; 2.38 mg of $CoSO_4.7 H_2O$ of analytical purity; 2.21 mg of NaF of analytical purity; 0.83 mg of $Na_2SeO_3.5 H_2O$ of analytical purity; 0.65 mg of KI of analytical purity; 0,25 mg $Na_2MoO_4.2 H_2O$ of analytical purity.

TABLE 4-continued

| Component | g/kg |
|---|---|

[2]Vitamin premix (quantities per kg of diet) 1.8 mg of retinal; 0.025 mg of cholecalciferol; 100 mg of D,L-α-tocopheryl acetate; 5 mg of menadione; 30 mg of ascorbic acid; 8 mg of thiamine mononitrate; 10 mg of riboflavin; 10 mg of pyridoxin; 40 mg of niacin; 30 mg of Ca-D-pantothenate; 3 mg of folic acid; 10 mg of p-aminobenzoic acid; 0.2 mg of biotin; 0.05 mg of cobalamine; 100 mg of myo-inositole; 1150 mg of choline chloride The experimental diets are mixed in a stainless steel precision mixer. The vitamin, trace element and phytase premixes are prepared in a laboratory mixer, corn starch being used in each case as carrier. The diets are stored at +4° C.

Table 5 shows the experimental design. 6 rats are used per experimental group. The mealy diets were administered ad lib. The amount of added zinc in the form of the zinc lipoate $Zn((R)-\alpha\text{-lipoate})_2(H_2O)_2$ is 10 mg/kg of feed (groups 1 and 2) and 20 mg/kg of feed (group 3). By partially replacing the corn starch by 0.4% by weight in the form of NAPA, molar PA:Zn ratios of 19.8:1 and 39.6:1 were established. The control group (group 1) received the PA-free base diet.

TABLE 5

| Group | Number of animals [n] | Amount of Zn as Zn lipoate [mg/kg] of diet | PA (% by weight) | PA:Zn (molar) |
|---|---|---|---|---|
| 1 | 6 | 10 | — | — |
| 2 | 6 | 10 | 0.4 | 39.6:1 |
| 3 | 6 | 20 | 0.4 | 19.8:1 |

4.3 Measuring the bioavailability parameters—production and preparation of the analytical material 4.3.1 Fecal and urine samples The amounts of feces and urine produced separately in the metabolic cages are collected quantitatively every day and stored at −22° C. To avoid any losses of N in the urine collection vessels, 1 ml of 20% strength HCl (Suprapur) is added to each of the vessels daily. For further analysis, the sample material is freeze-dried for 48 h.

4.3.2 Organ and tissue samples

The right femur, liver and testes are removed immediately after decapitation and complete exsanguination of the animals and the fresh mass is determined. The samples are sealed in plastic film and stored at −22° C. until further analysis.

4.3.3 Blood

The rats are decapitated at the end of the experiment after complete narcosis with chloroform and the blood collected in heparinized plastic tubes. 40 I.U. of heparin sodium are introduced per ml of blood.

Immediately after sampling, the blood samples are centrifuged for 15 minutes at 16000 g and the plasma is pipetted into 2 ml test tubes. The samples were stored at −80° C. until further analysis.

4.4 Preparation of the ash solutions and Zn determination

The samples of diet, feces, urine and tissue are dry-ashed exclusively. The glassware used is cleaned with 20% strength $HNO_3$ (analytical grade) before use and rinsed repeatedly with twice-distilled water. The quartz crucibles are preignited overnight at 750° C. in a muffle furnace.

The samples are dry-ashed for 18 h at 450° C.

After ashing, 3M HCl (Suprapur) added to the samples, which are covered with a watch glass and heated for 10 minutes on a boiling water bath. The volumes of acid added depend on the amount of ash solutions to be prepared which in each case should be in a final concentration of 0.3 M. After cooling, the samples are filtered with hot twice-distilled water through an ash-free round filter into a volumetric flask with a ground glass joint. Incompletely ashed samples are kept in polyethylene bottles until further analysis.

Zinc is determined by means of atomic absorption spectrophotometry (AAS) in an acetylene flame.

4.5 Diagnosis of zinc status 4.5.1 Determination of the plasma zinc concentration The plasma zinc concentration is measured directly in the flame by means of AAS (Philips, PIJ 9400). The samples are diluted with 0.1 M HCl in a ratio of 1:20 (v/v).

4.5.2 Determination of the free zinc binding capacity

The percentage free zinc binding capacity is determined by the method of KINCAID and CRONRATH (J. Dairy Sci. 62 (1979) 120, 1474–1479) in the modification by ROTH and KIRCHGESSNER (Res. Exp. Med. 177 (1980), 213–219). To use the limited volume of plasma effectively, the individual working steps are changed as follows: to 0.4 ml of plasma is added the same volume of a $ZnCl_2$ solution (5 µg Zn/ml) (saturation of free Zn binding positions of the plasma proteins). To precipitate the excess non-protein-bound zinc, 40 mg of basic magnesium carbonate are added. After centrifuging the samples, 0.4 ml of the Zn-saturated plasma in the supernatant is pipetted off and 0.6 ml of 0.1 M HCl is added. Zn is determined by AAS directly in the flame. The free Zn binding capacity is calculated from the difference between the Zn content of the saturated plasma and untreated plasma, with the Zn concentration of the saturated plasma being used as a basis for the reference parameter.

4.5.3 Determination of alkaline phosphatase activity

The activity of the Zn metalloenzyme alkaline phosphatase (E.C. 3.1.3.1) is determined, using the individual chemicals diethanolamine buffer and p-nitrophenyl phosphate, under the recommendations of the DEUTSCHE GESELLSCHAFT FÜR KLINISCHE CHEMIE (Z. Klin. Chem. u. klin. Biochem. 10 (1972), 191):

AP catalyzes the following reaction:

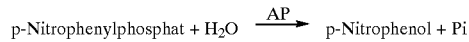

The enzyme activity is measured kinetically on a semimicroscale at a wavelength of 405 nm and 25° C. using a UV spectrophotometer. All series analyses include a control serum having values in the normal physiological range.

Comparison Example 1

Study 2: Bioavailability of $ZnSO_4$ in Rats

The experiments were carried and evaluated in a similar manner to Example 4 using $ZnSO_4$ as Zn source. Table 6 shows the experimental design. 6 rats are used per experimental group. The mealy diets are administered ad lib. The amount of zinc added in the form of zinc sulfate is 10 mg/kg of feed (groups 4 and 5) and 20 mg/kg of feed (group 6). By partially replacing the corn starch with 0.4% by weight of NaPA, molar PA:Zn ratios of 19.8:1 and 39.6:1 are established. The control group (group 1) received the PA-free base diet.

TABLE 6

| Group | Number of animals [n] | Amount of Zn as $ZnSO_4$ [mg/kg] diet | PA (% by weight) | PA:Zn (molar) |
|---|---|---|---|---|
| 4 | 6 | 10 | — | — |
| 5 | 6 | 10 | 0.4 | 39.6:1 |
| 6 | 6 | 20 | 0.4 | 19.8:1 |

Evaluation of the results from Example 4 (Study 1) and Comparison Example 1 (Study 2)

The addition of NaPA led to typical zinc deficiency symptoms such as anorexia, alopecia and depression of growth. These effects are less strongly expressed at an addition rate of 20 mg of Zn/kg of feed than at a dosage of 10 mg/kg.

In the direct comparison of Zn lipoate (Example 4) and zinc sulfate (Comparison Example 1), a marked superiority of lipoate was found, since the deficiency symptoms are still present with the sulfate, whereas these disappear completely at the high dose of zinc lipoate.

The apparent absorption and retention of Zn from zinc lipoate is increased at both dosages.

In a similar manner to the apparent Zn absorption and retention, various Zn status parameters of blood plasma are improved by Zn lipoate in comparison with Zn sulfate (Zn concentration, free zinc binding capacity, alkaline phosphatase activity) and femur and liver Zn concentration.

Overall, it may be concluded that zinc lipoates beneficially affect virtually all parameters which are suitable for diagnosing the Zn status, compared with zinc sulfate, which documents an increased bioavailability.

EXAMPLE 5

Comparison Example 2

Study 3: Bioavailability Investigations of $Zn((R)-\alpha-Lipoat)_2-(H_2O)_2$ in Rats Compared with the Bioavailability of Zinc Sulfate 5.1 Experimental design 36 male Wistar albino rats (Harlan Winkelmann, Borchen) having an initial weight of 47.0±2.63 g were randomly divided into 6 groups each of 6 animals and fed the diets specified in Table 7 (experimental design) and Section 5.2 over a period of 28 days. The animals were kept individually in Makrolon cages on stainless grids under standard conditions (22° C., 55% relative humidity, 12 hour light/dark rhythm). Feed and deionized drinking water were available to the experimental animals ad libitum. During the 2nd and 3rd experimental week (metabolism phase) feces were collected quantitatively. After completion of the experimental phase (day 28), the animals were decapitated under $CO_2$— anesthesia, exsanguinated and the tissue to be analyzed was removed. Groups Ib, IIb and IIIb here are Example 5, while Groups Ia, IIa and IIIa are Comparison Example 2.

TABLE 7

| Group | No. of animals (n) | Zn (mg/kg) | Zn compound | Phytic acid (0.4% as NaPA) |
|---|---|---|---|---|
| Ia | 6 | 10 | Zn sulfate | − |
| Ib | 6 | 10 | Zn lipoate | − |
| IIa | 6 | 10 | Zn sulfate | + |
| IIb | 6 | 10 | Zn lipoate | + |

TABLE 7-continued

| Group | No. of animals (n) | Zn (mg/kg) | Zn compound | Phytic acid (0.4% as NaPA) |
|---|---|---|---|---|
| IIIa | 6 | 20 | Zn sulfate | + |
| IIIb | 6 | 20 | Zn lipoate | + |

$\Sigma = 36$

Parameters used to estimate Zn availability were the zootechnical parameters feed intake, live weight development and live weight increase, apparent Zn absorption, alkaline phosphatase activity in plasma, plasma and femur Zn concentration and metallothionin concentration in liver tissue.

5.2 Experimental diets

The experimental animals were fed semisynthetic diets based on high-purity components (corn starch, egg albumin protein, sucrose, soybean oil and cellulose) over a period of 28 days (see Table 8 for composition of the base diet), the experimental diets differing with respect to the type of zinc compound supplemented, the absolute Zn concentration and the phytic acid content (0.4% PA from NaPA, Sigma-Aldrich, Steinheim) (see Table 7).

Zn supplements used were Zn $((R)\text{-}\alpha\text{-Lipoat})_2(H_2O)_2$ from Example 1 (Example 5) and Zn sulfate ($ZnSO_4.7 H_2O$ analytical grade, Merck, Darmstadt) (Comparison Example 2). The Zn concentrations of the experimental diets Ia–IIb were set at a level of 10 mg/kg of diet estimated to be marginal for growing rats, in order to enable investigation of the availability of the Zn supplements under test in the suboptimun supply range. The currently recommended allowances of the NATIONAL RESEARCH COUNCIL for growing laboratory rats are 12 mg of Zn per kg of diet (NRC 1995), provided that the diet does not contain phytate.

TABLE 8

| Component | g/kg |
|---|---|
| Corn starch | 477 |
| Egg albumin protein | 200 |
| Sucrose | 100 |
| Soybean oil | 70 |
| Cellulose | 30 |
| L-lysine HCl | 3 |
| Mineral premix[1] | 100 |
| Vitamin premix[2] | 20 |
| | 1000 |

[1]Mineral premix (figures per kg of diet): 16.17 g $CaHPO_4.2 H_2O$; 8.91 g $K_2HPO_4$; 8.08 $CaCO_3$; 6.08 g $MSO_4.7 H_2O$; 1.16 g NaCl; 0.58 g $Na_2CO_3$; 298.68 mg $FeSO_4.7 H_2O$; 61.52 mg $MnSO_4.H_2O$; 31.45 mg $CuSO_4.5 H_2O$; 9.61 mg $KCr(SO_4)_2.12 H_2O$; 2.38 mg $CoSO_4.7 H_2O$; 2.21 mg NaF; 0.83 $Na_2SeO_3.5 H_2O$; 0.52 mg KI; 0.50 mg $NaMoO_4.2 H_2O$
[2]Vitamin premix (figures per kg of diet); 4500 IU Vitamin A; 1100 IU Vitamin $D_3$; 80 IU Vitamin E; 0.9 mg of Menadione; 30 mg of ascorbic acid; 6 mg of thiamin; 7 mg of riboflavin; 7 mg of pyridoxin; 0.03 mg of cobalamin; 0.25 mg of biotin; 2.5 mg of folic acid; 35 mg of nicotinic acid; 20 mg of pantothenic acid; 1100 mg of choline chloride; 100 mg of inositol; 10 mg of p-aminobenzoic acid Except for the specified Zn step of 10 mg/kg of diet, the sought-after diet concentrations of minerals (Table 9: Sought-after concentrations of major elements and trace elements of experimental diets and recommendations of the NRC for growing laboratory rats) and of vitamins are always significantly higher than the recommendations of the NATIONAL RESEARCH COUNCIL for growing laboratory rats (NRC 1995) and may therefore be estimated as reliably covering requirements.

Table 9 shows the sought-after concentrations of major and trace elements of the experimental diets and recommendations of the NRC for growing laboratory rats (NRC 1995)

TABLE 9

| Major elements | Sought-after (g/kg) | NRC (g/kg) | Trace elements | Sought-after mg/kg | NRC (mg/kg) |
|---|---|---|---|---|---|
| Calcium | 7.0 | 5.0 | Iron | 60 | 35 |
| Phosphorus | 4.5 | 3.0 | Manganese | 20 | 10 |
| Magnesium | 0.6 | 0.5 | Zinc | 10/20 | 12 |

5.3 Analytical methods

5.3.1 Analysis of diets

Dry matter and crude nutrients (crude protein, crude fat, crude fiber, crude ash) were determined according to the provisions of the VDLUFA-Methodenbuch zur chemischen Untersuchung von Futtermitteln [VDLUFA Methods for Chemical Analysis of Feedstuffs] (NAUMANN, C.; BASSLER, R. (1997): Method Manual Volume III. Die chemische Untersuchung von Futtermitteln [Chemical Analysis of Feedstuffs], 4th supplement VDLUFA Verlag, Darmstadt). The gross energy content of the experimental diets was determined using an adiabatic bomb calorimeter (IKA calorimeter C400, Jahnke und Kunkel, Staufen).

Phytic acid concentration was determined quantitatively in the experimental diets by means of HPLC using the method of NEUSSER and PALLAUF (NEUSSER, H.; PALLAUF, J. (1988): Bestimmung von Phytinsäure in Futtermitteln und Faeces mittels Hochdruckflüssigkeits-Chromatographie [Determination of Phytic Acid in Feeds and feces using High-pressure Liquid Chromatography]. J. Anim. Physiol. a. Anim. Nutr. 60, 20.).

The diet samples were ashed using the dry ashing method. In this case the organic matrix was thermally decomposed and completely mineralized. The number of ashed parallel samples per diet was n=2. The ash residue was brought into solution by addition of acid and was then quantitatively analyzed. The concentrations of Ca, Mg, P, Fe and Mn in the diets were determined using ICP-AES (PU 701, Unicam, Kassel), Zn concentrations were determined by flame AAS (Philips, PU 9400, Kassel). The analyses were confirmed by standard addition.

5.3.2 Zn concentration in the femur

The ash solutions were prepared by the principle of wet ashing. The sample material was admixed with 10 ml of 65% strength $HNO_3$ (Merck, Suprapur) and then boiled under a reflux condenser in a digestion apparatus (Gerhardt SMA-20, Bonn). This oxidatively degraded the organic matrix and completely mineralized the test material. The Zn concentration was determined in the ash solutions by flame-AAS (Philips, PU 9400, Kassel).

5.3.3 Analysis of the fecal samples

During the two-week metabolism phase, the rat feces were collected daily, adherent feed residues and other impurities were removed and the samples were stored at −20° C. At the end of the metabolism period the fecal weight was determined quantitatively and feces were then freeze-dried under vacuum over a period of 48 h (Gamma 1–20, Christ, Osterode). The dried samples were finely around using a domestic grinder (Moulinette electronic 89902) and stored at ambient temperature in PE bottles.

A sample aliquot of 1.5 g or the freeze-dried and ground fecal samples was dried for 24 h at 105° C. to remove residual water and then ashed in a muffle furnace at 450° C. for 21 h. The ash residue was dissolved by acid addition and then analyzed quantitatively. The Zn concentration in the fecal samples was determined by flame-AAS (Philips, PU 9400, Kassel).

5.3.4 Diagnosis of Zn status

Zn absorption was calculated, without taking into account endogenous level as a difference between element absorption and fecal excretion (=apparent absorption). Plasma Zn concentration was determined by AAS (Philips, PU 9400, Kassel). The samples were diluted with 0.1 M HCl in a ratio of 1:20 (v/v). The activity of the Zn metalloenzyme alkaline phosphatase (AP) (E.C. 3.1.3.1) wan assayed using the individual chemicals diethanolamine buffer and p-nitrophenyl phosphate according to the recommendations of the DEUTSCHE GESELLSCHAFT FÜR KLINIESCHE CHIMIE [German Clinical Chemistry Society] (DEUTSCHE GESELLSCHAFT FÜR KLINISCHE CHEMIE (1972). Standardmethode zur Bestimmung der Aktivität der alkalischen Phosphatase (AP) [Standard Method for Determining Alkaliur Phosphatase (AP) Activity]. Z. klin. Chem u. klin. Biochemie. 10, 191).

5.3.5 Metallothionin in liver tissue

Total MT concentration in liver tissue was determined using the cadmium-binding method of EATON and TOAL (EATON, D. L., TOAL, B. F. (1982): Evaluation of the cadmium/hemoglobin affinity assay for the rapid determination of metallothionein in biological tissues. Toxicol Appl. Pharmacol. 66, 134–142) in a modification tested at the Giessen Institute (LEUNERT, V. (1994): Einfluβ von Zink sowie fetalem Kälberserum, bovinem Serumalbumin und calciummobilisierenden Rezeptoragonlsten auf Metallothionein in primär kultivierten Rattenhepatocyten [Effect of zinc and fecal calf serum, vine serum albumin and calcium-immobilizing receptor agonists on metallothionin in primary cultivations of rat hepatocytes]. Inaugural dissertation at the Institut für Tierernährung und Ernährungse-physiologie [Institute of Animal Nutrition and Nutritional Physiology] of the University of Cicesen, Verlag Shaker, Aachen, PALLAUF et al. 1995). The protein content in liver homogenates war determined using the Lowry-Folin method (DAWSON, R. M. C. ELLIOTT, D C; JONES, K. M. (1986): Data for biochemical research, $3^{rd}$ ed., Clarendon Press, New York, 543).

5.3.5. Statistical analysis

Descriptive treatment and graphical plotting of the data material war carried oil using the spreadsheet program Microsoft Excel 2000. Statistical analysis of the experimental results war performed using SPSS (Statistical Package for the Social Sciences) for Widows (Version 10.0) and included testing for normal distribution (KOLKOCOROV-SMIPNOW- and SHAPIRO-WILKS Test) and variance homogeneity (LEVENE Test) and the single-factor variance analysis (UNITWAY procedure) with subsequent test significance of mean differences using TUKEY HSD. The level of significance was set at 5% ($p<0.05$). In the absence of variance homogeneity, significance of mean differences was tested using the GAMES HOWELL Test.

The results listed in the tables give the group mean (M) and the standard deviation (SD) of the individual values. Significant mean differences were indicated by different superscripts.

5.4. Results 5.4.1 Experimental diets

The experimentally determined contents of crude nutrients and the gross energy of the experimental diets are listed in Table 10. All diets, within the usual ranges of variation, had compatable contents of dry matter, crude protein, crude fat, crude fiber and gross energy. The increase in crude ash content in diets IIa–IIIb is due to the supply of phosphorus because of PA supplementation.

TABLE 10

Experimental Diets Ia–IIIb

| | | |
|---|---|---|
| Dry matter | (% of IM) | 91.6 ± 0.13 |
| Crude protein | (% of IM) | 16.7 ± 0.06 |
| Crude fat | (% of IM) | 7.16 ± 0.02 |
| Crude fiber | (% of IM) | 5.21 ± 0.48 |
| Crude ash (diets Ia, Ib) | (% of IM) | 4.31 ± 0.02 |
| Crude ash (diets IIa–IIIb) | (% of IM) | 4.85 ± 0.07 |
| Gross energy | (kJ/g of IM) | 17.8 ± 0.19 |

The mineral concentrations in the experimental diets are shown in Table 11. The element concentrations conformed within analytical variation. There was adequate agreement with the target values. Higher phosphorus contents in diets IIa–IIb were due to PA supplementation of 0.4%.

TABLE 11

| Diet | Ca (g/kg) | Mg (g/kg) | P (g/kg) | Fe (mg/kg) | Zn (mg/kg) | Mn (mg/kg) |
|---|---|---|---|---|---|---|
| Ia | 6.93 | 0.75 | 4.78 | 53.7 | 12.1 | 21.2 |
| Ib | 6.99 | 0.89 | 4.81 | 71.2 | 10.2 | 18.4 |
| IIa | 7.20 | 0.92 | 5.92 | 69.2 | 10.4 | 19.9 |
| IIb | 7.40 | 0.91 | 6.04 | 67.9 | 9.93 | 20.9 |
| IIIa | 7.44 | 0.81 | 6.20 | 78.2 | 19.9 | 20.0 |
| IIIb | 7.09 | 0.92 | 6.07 | 62.8 | 21.1 | 16.2 |

The phytic acid contents determined, molar PA: Zn ratios and PA×Ca: Zn ratios of the experimental diets are shown in Table 12. The PA concentrations corresponded to the expected values and conformed within analytical variation.

TABLE 12

| Diet | PA (%) | PA:Zn (molar) | PA x Ca:Zn (molar) |
|---|---|---|---|
| Ia | n.d. | — | — |
| Ib | n.d. | — | — |
| IIa | 0.40 | 38.7 | 6.96 |
| IIb | 0.39 | 38.4 | 7.11 |
| IIIa | 0.41 | 20.4 | 3.79 |
| IIIb | 0.40 | 18.9 | 3.35 |

5.4.2 Zootechnical parameters

The mean weekly feed intake and total feed intake during the 28-day experimental period are shown in Table 13. When PA-containing diets having a low Zn level (groups IIa and IIb) were fed, significantly lower total feed intake was observed compared with groups Ia and Ib and IIIa and IIIb. An increase owing to Zn-α-lipoate feeding was observed.

The lowest growth of rats was observed when PA-containing diets having low Zn concentrations were fed (groups Ia and IIb) (Table 14). Not only offering PA-free diets having a low Zn level (groups Ia and Ib) but also offering PA-containing diets having relatively high Zn concentration (groups IIIa and IIIb) resulted in a significantly improved live weight gain. In addition, in each case an increase in live weight gain was observed due to Zn lipoate compared with Zn sulfate.

Table 13 shows the feed intake per week (g) and total feed intake (g/28d) of growing rats with addition of Zn sulfate, Zn lipoate and phytic acid (PA) (n=6×6). Different superscripts within a column indicate significant differences of at least $p<0.05$ (Tukey-HSD), different superscripts shown in italics within a column show significant differences of at least $p<0.05$ (Games Howell)

TABLE 13

Feed Intake

| Group | | $d_1$–$d_7$ | $d_8$–$d_{14}$ | $d_{15}$–$d_{21}$ | $d_{22}$–$d_{28}$ | Total |
|---|---|---|---|---|---|---|
| Ia, 10 ppm Zn | M | 40.4 ab | 67.8 bc | 77.5 bc | 86.6 b | 272 b |
| (Sulfate) | SD | ±20.9 | ±12.9 | ±12.4 | ±6.93 | ±50.7 |
| Ib, 10 ppm Zn | M | 54.9 ab | 78.7 c | 86.9 c | 86.5 b | 307 b |
| (Lipoate) | SD | ±11.8 | ±5.82 | ±5.27 | ±5.20 | ±17.4 |
| IIa, 10 ppm Zn | M | 37.4 a | 42.3 a | 40.5 a | 45.3 a | 166 a |
| (Sulfate) + PA | SD | ±11.3 | ±8.30 | ±4.40 | ±7.30 | ±25.2 |
| IIb, 10 ppm Zn | M | 39.5 ab | 46.5 a | 48.2 a | 51.3 a | 186 a |
| (Lipoate) + PA | SD | ±14.3 | ±4.49 | ±6.17 | ±4.18 | ±20.8 |
| IIIa, 20 ppm Zn | M | 49.6 ab | 61.0 b | 67.9 b | 74.8 b | 253 b |
| (Sulfate) + PA | SD | ±15.9 | ±7.75 | ±10.2 | ±10.6 | ±38.2 |
| IIIb, 20 ppm Zn | M | 60.0 b | 77.3 c | 79.2 bc | 83.5 b | 300 b |
| (Lipoate) + PA | SD | ±3.86 | ±6.63 | ±8.25 | ±6.76 | ±22.5 |

Table 14 shows the changes in live weight and live weight gains of growing rats with supply of Zn sulfate, Zn lipoate and phytic acid (PA) (n=6×6). Different superscripts within a column indicate significant differences of at least p<0.05 (Tukey-HSD), different superscripts shown in italics within a column show significant differences of at least p<0.05 (Games Howell).

TABLE 14

| Group | | | Live Weight (g) | | | | | |
|---|---|---|---|---|---|---|---|---|
| | | | $d_0$ | $d_7$ | $d_{14}$ | $d_{21}$ | $d_{28}$ | LW Gain |
| Ia. | 10 ppm Zn (Sulfate) | M | 47.3 x | 58.1ab | 104.2ab | 141.3bc | 175.8bc | 128.5bc |
| | | SD | ±3.38 | ±20.5 | ±21.5 | ±21.5 | ±17.4 | ±20.0 |
| Ib. | 10 ppm Zn (Lipoate) | M | 47.1 | 75.6ab | 122.5b | 159.2c | 185.8c | 138.7c |
| | | SD | ±3.01 | ±8.96 | ±8.36 | ±7.63 | ±7.22 | ±7.68 |
| IIa. | 10 ppm Zn (Sulfate) + PA | M | 45.8 | 62.0a | 84.6a | 94.2a | 106.5a | 60.7a |
| | | SD | ±2.78 | ±5.47 | ±13.2 | ±13.7 | ±15.4 | ±13.4 |
| IIb. | 10 ppm Zn (Lipoate) + PA | M | 47.2 | 60.0ab | 82.5a | 99.1a | 114.2a | 67.0a |
| | | SD | ±2.52 | ±14.3 | ±11.2 | ±10.4 | ±8.39 | ±6.31 |
| IIIa. | 20 ppm Zn (Sulfate) + PA | M | 47.2 | 68.4ab | 102.4ab | 132.3b | 161.9b | 114.7b |
| | | SD | ±2.49 | ±15.9 | ±12.1 | ±14.7 | ±14.9 | ±15.4 |
| IIIb. | 20 ppm Zn (Lipoate) + PA | M | 47.3 | 77.9b | 119.1b | 147.4bc | 173.2bc | 125.9bc |
| | | SD | ±2.36 | ±4.57 | ±9.00 | ±12.3 | ±11.4 | ±10.4 |

5.4.3 parameters of zinc availability and zinc status

In the course of the 14-day metabolism phase, the Zn intake of groups IIa and IIb (10 mg of Zn/kg of diet+0.4% PA) was significantly lower than Zn intake of groups Ia and Ib (Table 15). When the dietary Zn concentration was increased to 20 mg per kg of diet (IIIa, IIIb), this achieved a significant increase in Zn supply by approximately the factor 2. Furthermore, when PA-containing diets having a high Zn level (20 mg/kg of diet) were offered, there was a significantly higher Zn intake owing to Zn lipoate supplementation.

Independently of PA supplementation, fecal Zn excretion of groups Ia, Ib, IIa and IIb was at a level of 0.411–0.494 mg/14 d (Table 15). Zn excretion via feces reached a significantly higher level (1.43–1.71 mg/14 d) owing to the dietary Zn concentration of 20 mg/kg than in groups having a lower Zn level.

The absolute apparent absorption (mg of Zn/14 d) was 1.24 and 1.35 mg/14 d for the rats fed with PA-free diets (groups Ia and Ib) (Table 15). When 0.4% PA was fed (groups Ia, IIb), a drastic reduction in Zn absorption to values of 0.351 and 0.446 mg/14 d was seen. When the Zn level was doubled to 20 mg/kg of diet (groups IIIa and IIIb), despite a PA content of 0.4%, an increase in absolute Zn absorption to values of 1.13 and 1.60 mg/14 d was seen. Within these two groups, there was a statistically significant higher absolute Zn absorption in the group with Zn lipoate (1.60 mg/14 d).

In the case of groups Ia and Ib fed PA-free diets, a high apparent Zn absorption of 73.6 to 76.4% was reached. After addition of PA, the percentage Zn absorption of the remaining groups (IIa to IIIb), regardless of the absolute Zn concentration, was at a statistically comparable level at 43.0 to 48.4%. However, an increase in apparent Zn absorption from group IIa to group IIb was found and from group IIIa to group IIIb owing to the Zn lipoate supplementation.

Table 15 shows the intake, fecal excretion and apparent absorption of zinc of growing rats on addition of Zn sulfate, Zn lipoate and phytic acid (PA) (n=6×6). Different superscripts within a column indicate significant differences of at least p<0.05 (Tukey-HSD), different superscripts shown in italics within a column indicate significant differences of at least p<0.05 (Games Howell)

TABLE 15

| Group | | Intake (mg/14 d) | Fecal excretion (mg/14 d) | Apparent absorption (mg/14 d) | Apparent absorption (%) |
|---|---|---|---|---|---|
| Ia, 10 ppm Zn | M | 1.76 b | 0.411 a | 1.35 bc | 76.4 b |
| (Sulfate) | SD | ±0.305 | ±0.122 | ±0.280 | ±7.33 |
| Ib, 10 ppm Zn | M | 1.68 b | 0.445 a | 1.24 b | 73.6 b |
| (Lipoate) | SD | ±0.106 | ±0.080 | ±0.092 | ±4.11 |
| IIa, 10 ppm Zn | M | 0.836 a | 0.484 a | 0.351 a | 43.0 a |
| (Sulfate) + PA | SD | ±0.146 | ±0.162 | ±0.038 | ±8.66 |
| IIb, 10 ppm Zn | M | 0.941 a | 0.494 a | 0.446 a | 47.3 a |
| (Lipoate) + PA | SD | ±0.099 | ±0.059 | ±0.078 | ±5.23 |
| IIIa, 20 ppm Zn | M | 2.57 c | 1.43 b | 1.13 b | 43.9 a |
| (Sulfate) + PA | SD | ±0.334 | ±0.170 | ±0.219 | ±4.63 |
| IIIb, 20 ppm Zn | M | 3.30 d | 1.71 b | 1.60 c | 48.4 a |
| (Lipoate) + PA | SD | ±0.308 | ±0.231 | ±0.199 | ±4.55 |

When PA-free diets having suboptimum Zn concentrations were offered (groups Ia and Ib), a high incorporation of Zn into the femur tissue of the rats was found (Table 16). After addition of 0.4% PA (groups IIa and IIb), in contrast, a drastic and significant reduction in bone Zn contents was observed. After doubling the dietary Zn level (groups IIIa and IIIb), a significant increase in Zn concentration in the femur to a mean level was observed. Zn lipoate, compared with Zn sulfate, with addition of phytate, showed a beneficial effect on the level of Zn incorporation into the femur tissue.

Comparable results were also found for the Zn concentration in plasma. Thus the plasma Zn concentration was at a high level when PA-free diets having a low Zn level were offered, whereas when 0.4% PA was added, the plasma contents were significantly reduced. A renewed partially significant increase in these values could be seen when the dietary Zn concentration was doubled to 20 mg per kg of diet.

Comparable changes were also found with respect to alkaline phosphatase activity in plasma. Thus the activity of the Zn-dependent enzyme when PA-free diets were offered, despite the low Zn content of the diets, was at a high level, whereas when 0.4% PA was added, a significant decrease in activity in groups IIa and IIb could be seen After the dietary Zn concentration was increased to 20 mg per kg of diet, an increase in enzyme activity to a level comparable to that of groups Ia and Ib was found.

Table 16 shows the Zn concentrations in femur and plasma and alkaline phosphatase activity in plasma of growing rats on addition of Zn sulfate, Zn lipoate and phytic acid (PA) (n=6×6). Different superscripts within a column indicate significant differences of at least p<0.05 (Tukey-HSD)

TABLE 16

| Group | | Femur ($\mu$g/g FW) | Plasma ($\mu$g/ml) | Alkaline Phosphatase (mU/ml Plasma) |
|---|---|---|---|---|
| Ia, 10 ppm Zn(Sulfate) | M | 81.4 [c] | 1.11 [bc] | 383 [b] |
| | SD | ±4.60 | ±0.24 | ±52.0 |
| Ib, 10 ppm Zn(Lipoate) | M | 79.2 [c] | 1.24 [c] | 365 [b] |
| | SD | ±8.00 | ±0.24 | ±54.6 |
| IIa, 10 ppm Zn (Sulfate) + PA | M | 36.3 [a] | 0.57 [a] | 216 [a] |
| | SD | ±4.74 | ±0.18 | ±53.4 |
| IIb, 10 ppm Zn (Lipoate) + PA | M | 41.2 [a] | 0.50 [a] | 225 [a] |
| | SD | ±4.72 | ±0.15 | ±38.1 |
| IIIa, 20 ppm Zn (Sulfate) + PA | M | 55.4 [b] | 0.80 [ac] | 347 [b] |
| | SD | ±9.53 | ±0.25 | ±42.0 |
| IIIb, 20 ppm Zn (Lipoate) + PA | M | 64.1 [b] | 0.96 [bc] | 384 [b] |
| | SD | ±10.1 | ±0.18 | ±62.8 |

At the metallothionin concentration measured in the liver tissue, in all groups (I, II and III) there were nominal increases in hepatic MT concentration, when the Zn source was Zn lipoate and not $ZnSO_4$.

Table 17 shows the metallothionin concentration in liver tissue of growing rats on addition of Zn sulfate, Zn lipoate and phytic acid (PA) (n=6×6).

TABLE 17

| Group | | Metallothionin (ng MT/mg Protein) |
|---|---|---|
| Ia, 10 ppm Zn(Sulfate) | M | 8.08 |
| | SD | ±2.71 |
| Ib, 10 ppm Zn(Lipoate) | M | 8.32 |
| | SD | ±4.16 |
| IIa, 10 ppm Zn(Sulfate) + PA | M | 6.36 |
| | SD | ±4.66 |
| IIb, 10 ppm Zn(Lipoate) + PA | M | 7.94 |
| | SD | ±2.29 |
| IIIa, 20 ppm Zn(Sulfate) + PA | M | 7.58 |
| | SD | ±3.15 |
| IIIb, 20 ppm Zn(Lipoate) + PA | M | 8.71 |
| | SD | ±6.46 |

We claim:

1. A method of increasing the bioavailabilty of mineral salts which comprises combining said salts and α-lipoic acid or α-dihydrolipoic acid.

2. The method of claim 1, wherein at least one mineral salt is combined with a-lipo acid or a-dihydrolpoic acid.

3. The method of claim 2, wherein the mineral salts have the formula I, $$(M)_n(B)_m \quad \text{I}$$

where
- M is a monovalent to trivalent physiologically acceptable metal cation,
- B is a monovalent to trivalent physiologically acceptable anion,
- n is 1, 2 or 3 and
- m is 1, 2 or 3, where the subscripts n and m correspond to the valency and charge equalization of the mineral salt of the formula I.

4. The method of claim 1, wherein the combination is metal α-lipoates, metal α-dihydrolioates or metal-α-lipoic acid complexes.

5. The method of claim 4, wherein the combination is α-lipoates, metal α-dihydrolipoates or metal-α-lipoic acid complexes of the formula II, $$(m)_w(Lp)_x(A)_y(H_2O)_z \quad \text{II}$$

where
- M is a monovalent to trivalent physiologically acceptable metal cation or a mixture of monovalent to trivalent physiologically acceptable metal cations,
- Lp is racemic α-lipoic acid or α-dihydrolipoic acid, (R)- or (S)-α-lipoic acid or (R)- or (S)-α-dihydrolipoic acid, racemic α-lipoate or dihydro-α-lipoate or (R)- or (S)-α-lipoateor (R)- or (S)-dihydro-α-lipoate,
- A is a physiologically acceptable monovalent or divalent anion,
- w is 1, 2, 3 or 4,
- x is 0, 1, or 4,
- y is 0, 1, 3, 4, 5 or 6, where the subscripts w, x and y correspond to the valency and charge equalization of the compound of the formula II.

6. The method of claim 1, wherein the α-lipoic acid is R-α-lipoic acid or the α-lipoate is (R)-α-lipoate.

7. A method of increasing the bioavailability of mineral salts in feedstuff or food supplements which comprises adding to said feedstuff or food supplements an effective amount of the metal α-lipoates, metal-α-lipoic acid complexes defined in claim 5.

8. A method of providing improving cosmetic formulations which comprises adding to said formulations an effective amount of the metal α-lipoates, metal-α-lipoic acid complexes defined in claim 5.

9. A method of providing improving drugs that are used to treat disorders in which lipoic acid has a therapeutic or prophylactic effect and in which there is a mineral salt deficiency which comprises adding to said drugs an effective amount of the metal α-dihydrolipoates or metal-α-lipoic acid complexes defined in claim 5.

10. A method of providing improving compositions for treating diabetes, tumors, HIV infections, AIDS, renal insufficiency, malnutrition, protein-energy malnutrition and mineral deficiencies which comprises adding to said compositions the metal α-lipoates, metal α-dihydrolipoates or metal-α-lipoic acid complexes defined in claim 5.

11. The method of claim 1 wherein the mineral salts are selected from the group consisting of Fe, Cr, Co, and Mn salts.

12. The method of claim 5 wherein M is a metal cation selected from the group consisting of cations of Fe, Cr, Co and Mn.

13. A composition comprising (R)-α-lipoic acid and at least one mineral salt selected from the group consisting of Fe, Cr, Co and Mn salts.

14. A metal α-lipoate, metal α-dihydrolipoate or metal-α-lipoic acid complex of the formula II', $$(M)_w(Lp)_x(A)_y(H_2O)_z \qquad \text{II'}$$

where

M is a metal cation selected from the group consisting of cations of Fe, Cr, Co and Mn, Lp is racemic α-lipoic acid or α-dihydrolipoic acid, (R)- or (S)-α-lipoic acid or (R)- or (S)-α-dihydolipoic acid, racemic α-lipoate or dihydro-α-lipoate or (R)- or (S)-α-lipoate or (R)- or (S)-dihydro-α-lipoate, A is a physiologically acceptable monovalent or divalent anion, w is 1 or 2, x is 1, 2, 3 or 4, y is 0, 1, 2, 3, 4, 5 or 6, where the subscripts w, x and y correspond to the valency and charge equalization and the following compounds are excluded:

$$\text{Mn}(Lip^-)ClO_4, FE_2DHL_{rac}2-)_3,$$

where $Lip^-$ is monovalent negative racemic or (R)- or (S)-α-lipoate, $Lip_{rac}$++ is monovalent negative racemic α-lipoate, $Lip_{rac}$ is racemic α-lipoic acid and $DHL_{rac}$2+—is divalent negative racemic α-dihydrolipoate.

15. A composition comprising metal α-lipoates, metal α-dihydrolipoates or metal-α-lipoic acid complexes as claimed in claim 14.

16. The metal-α-lipoate, metal α-dihydrolipoate or metal-α-lipoic acid complex defined in claim 5, wherein M is a metal cation selected from the group consisting of cations of Fe, Cr, Co and Mn.

17. A composition comprising metal α-lipoates, metal α-dihydrolipoates or metal-α-lipoic acid complexes as claimed in claim 16 and α-lipoic acid or α-dihydrolipoic acid.

* * * * *

UNITED STATES PATENT AND TRADEMARK OFFICE
CERTIFICATE OF CORRECTION

PATENT NO. : 6,887,894 B2
APPLICATION NO. : 09/897922
DATED : May 3, 2005
INVENTOR(S) : Kramer et al.

It is certified that error appears in the above-identified patent and that said Letters Patent is hereby corrected as shown below:

On the title page item (30), Foreign Application Priority Data, please delete:

"Jul. 7, 2001 (DE) 101 32 601"

In Claim 5, column 20, lines 20-21, please delete:
"wherein the combination is α-lipoates" and please substitute therefore:

-- wherein the combination is metal α-lipoates --

In Claim 5, column 20, lines 36-39, please delete:
"w is 1, 2, 3, or 4,
 x is 0, 1, or 4
 y is 0, 1, 3, 4, 5 or 6," and please substitute therefore:

-- w is 1 or 2
 x is 1, 2, 3 or 4
 y is 1, 2 or 3 and
 z is 0, 1, 2, 3, 4, 5, or 6, --

In Claim 7, column 20, lines 47-48, please delete:
"metal α-lipoates, metal-α-lipoic acid complexes" and please substitute therefore:

-- metal α-lipoates, metal α-dihydrolipoates or metal-α-lipoic acid complexes --

In Claim 8, column 20, line 49, please delete:
"improving"

In Claim 8, column 20, lines 51-52, please delete:
"metal α-lipoates, metal-α-lipoic acid complexes" and please substitute therefore:

-- metal α-lipoates, metal α-dihydrolipoates or metal-α-lipoic acid complexes --

UNITED STATES PATENT AND TRADEMARK OFFICE
CERTIFICATE OF CORRECTION

PATENT NO. : 6,887,894 B2
APPLICATION NO. : 09/897922
DATED : May 3, 2005
INVENTOR(S) : Kramer et al.

It is certified that error appears in the above-identified patent and that said Letters Patent is hereby corrected as shown below:

In Claim 9, column 20, line 53, please delete:
"improving"

In Claim 9, column 20, lines 57-58, please delete:
"metal α-dihydrolipoates or metal-α-lipoic acid complexes" and please substitute therefore:

-- metal α-lipoates, metal α-dihydrolipoates or metal-α-lipoic acid complexes --

In Claim 10, column 20, line 59, please delete:
"improving"

In Claim 13, column 21, line 4, please delete:
"(R)-α-lipoic acid" and please substitute therefore:

-- (R)-α-lipoic acid or (S)-α-lipoic acid --

In Claim 14, column 21, line 23, please delete:
"y is 0, 1, 2, 3, 4, 5, or 6" and please substitute therefore:

-- y is 0, 1, 2 or 3 and
z is 0, 1, 2, 3, 4, 5, or 6 --

In Claim 14, column 22, line 9, please delete
"$Lip_{rac}++$" and please substitute therefore:

-- $Lip_{rac}-$ --

UNITED STATES PATENT AND TRADEMARK OFFICE
CERTIFICATE OF CORRECTION

PATENT NO. : 6,887,894 B2
APPLICATION NO. : 09/897922
DATED : May 3, 2005
INVENTOR(S) : Kramer et al.

It is certified that error appears in the above-identified patent and that said Letters Patent is hereby corrected as shown below:

In Claim 14, column 22, line 11, please delete
"$DHL_{rac}2++-$" and please substitute therefore:

-- $DHL_{rac}2-$ --

Signed and Sealed this

Sixth Day of May, 2008

JON W. DUDAS
*Director of the United States Patent and Trademark Office*